US010065187B2

(12) United States Patent
Sieben et al.

(10) Patent No.: US 10,065,187 B2
(45) Date of Patent: Sep. 4, 2018

(54) CENTRIFUGAL PLATFORM AND DEVICE FOR RAPID ANALYSIS OF OILFIELD FLUIDS

(71) Applicant: SCHLUMBERGER TECHNOLOGY CORPORATION, Sugar Land, TX (US)

(72) Inventors: Vincent Joseph Sieben, Cambridge, MA (US); Cedric Floquet, Cambridge, MA (US); Farshid Mostowfi, Boston, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 177 days.

(21) Appl. No.: 15/043,082

(22) Filed: Feb. 12, 2016

(65) Prior Publication Data

US 2017/0232435 A1 Aug. 17, 2017

(51) Int. Cl.
*B01L 3/00* (2006.01)
*G01N 21/07* (2006.01)
(Continued)

(52) U.S. Cl.
CPC ......... *B01L 3/50273* (2013.01); *B01L 3/5027* (2013.01); *C09K 8/524* (2013.01);
(Continued)

(58) Field of Classification Search
CPC ......... B01L 2200/10; B01L 2300/0627; B01L 2300/0803; B01L 2300/087;
(Continued)

(56) References Cited

U.S. PATENT DOCUMENTS 8,380,444 B2 2/2013 Kim et al.
8,539,823 B2 9/2013 Lee
(Continued)

FOREIGN PATENT DOCUMENTS

WO WO2016209248 A1 12/2016

OTHER PUBLICATIONS

Jennings, David W. et al, "MS New Dead-Crude Oil Asphaltene Inhibitor Test Method," OTC-25113-MS (2014) 14 pages.
(Continued)

*Primary Examiner* — Jennifer Wecker

(57) ABSTRACT

A method of evaluating an asphaltene inhibitor includes providing a centrifugal microfluidic system including: a disc mounted to rotate about an axis; a microfluidic device mounted on the disc, the device having sample, solvent, inhibitor, and precipitant reservoirs and an analysis chamber in fluid communication with the sample, solvent, inhibitor, and precipitant reservoirs; and an optical detection system coupled to the analysis chamber and configured to measure the optical transmission of fluid in the analysis chamber. The method includes filling the sample, solvent, inhibitor, and precipitant reservoirs, respectively, with a sample, solvent, inhibitor, and precipitant; rotating the disc to generate centrifugal force to cause the sample, solvent, inhibitor, and precipitant to travel radially outward to the analysis chamber; and measuring the optical transmission of a mixture of the sample, solvent, inhibitor, and precipitant in the analysis chamber as a function of radial distance of the analysis chamber.

10 Claims, 6 Drawing Sheets

(51) Int. Cl.

| | |
|---|---|
| ***G01N 21/65*** | (2006.01) |
| ***G01N 33/22*** | (2006.01) |
| ***G01N 21/82*** | (2006.01) |
| ***C09K 8/524*** | (2006.01) |
| ***C10G 75/04*** | (2006.01) |
| ***G01N 21/25*** | (2006.01) |
| ***G01N 33/28*** | (2006.01) |
| ***G01N 21/64*** | (2006.01) |
| ***G01N 35/00*** | (2006.01) |
| *G01N 21/03* | (2006.01) |
| *G01N 21/77* | (2006.01) |

(52) U.S. Cl.

CPC ............. *C10G 75/04* (2013.01); *G01N 21/07* (2013.01); *G01N 21/253* (2013.01); *G01N 21/645* (2013.01); *G01N 21/65* (2013.01); *G01N 21/82* (2013.01); *G01N 33/22* (2013.01); *G01N 33/2823* (2013.01); *G01N 33/2835* (2013.01); *G01N 35/00069* (2013.01); *B01L 2200/10* (2013.01); *B01L 2300/0627* (2013.01); *B01L 2300/0803* (2013.01); *B01L 2300/087* (2013.01); *B01L 2400/0409* (2013.01); *G01N 21/0332* (2013.01); *G01N 2021/0328* (2013.01); *G01N 2021/0346* (2013.01); *G01N 2021/7783* (2013.01); *G01N 2021/7786* (2013.01)

(58) Field of Classification Search

CPC ........... B01L 2400/0409; B01L 3/5027; B01L 3/50273; C09K 8/524; C10G 75/04; G01N 2021/0328; G01N 2021/0346; G01N 2021/7783; G01N 2021/7786; G01N 21/0332; G01N 21/07; G01N 21/253; G01N 21/645; G01N 21/65; G01N 21/82; G01N 33/22; G01N 33/2823; G01N 33/2835; G01N 35/00069

See application file for complete search history.

(56) References Cited

U.S. PATENT DOCUMENTS

| | | | | |
|---|---|---|---|---|
| 8,580,567 | B2 | 11/2013 | Sarofim et al. | |
| 8,584,513 | B2 * | 11/2013 | Hough .................. | G01N 33/26 73/53.01 |
| 8,609,038 | B2 | 12/2013 | Kim et al. | |
| 2008/0108120 | A1 * | 5/2008 | Cho .................... | B01F 13/0059 435/173.7 |
| 2011/0020194 | A1 * | 1/2011 | Lee .................... | B01L 3/50273 422/400 |
| 2011/0269151 | A1 * | 11/2011 | Kim ...................... | B82Y 15/00 435/7.9 |
| 2014/0242721 | A1 * | 8/2014 | Kellogg .............. | G01N 33/543 436/501 |
| 2014/0328888 | A1 | 11/2014 | Jennings et al. | |
| 2015/0238955 | A1 | 8/2015 | Lee et al. | |
| 2017/0082551 | A1 | 3/2017 | Mackay et al. | |

OTHER PUBLICATIONS

Hwang, Hyundoo et al., "Lab-on-a-Disc for Simultaneous Determination of Nutrients in Water," ACS (2013) pp. 2954-2960.

Laboratory Screening Test to Determine the Ability of Scale Inhibitors to Prevent the Precipitation of Barium Sulfate or Strontium Sulfate, or Both for Solution (for Oil and Gas Production Systems); NACE Stander TM0197-2010 (2010) 9 pages.

Sieben, Vincent J. et al, "Microfluidic Colourimetric Chemical Analysis System: Application to Nitrite Detection," Analytical Methods (2010) vol. 2, pp. 484-491.

M. Czugala, R. Gorkin Iii, T. Phelan, J. Gaughran, V. F. Curto, J. Ducrée, D. Diamond and F. Benito-Lopez, "Optical sensing system based on wireless paired emitter detector diode device and ionogels for lab-on-a-disc water quality analysis" Lab on a Chip—Miniaturisation for Chemistry and Biology, 2012, 12, pp. 5069-5078.

M. Czugala, D. Maher, F. Collins, R. Burger, F. Hopfgartner, Y. Yang, J. Zhaou, J. Ducree, A. Smeaton, K. Fraser, F. Benito-Lopez and D. Diamond, "CMAS: fully integrated portable Centrifugal Microfluidic Analysis System for on-site colorimetric analysis" RSC Advances, 2013 (26 pages).

H. Hwang, Y. Kim, J. Cho, J.-Y. Lee, M.-S. C. Choi and Y.-K. Cho, "Lab-on-a-Disc for Simultaneous Determination of Nutrients in Water" Analytical Chemistry, Jan. 15, 2013, 85(5), pp. 2954-2960.

M. C. R. Kong and E. D. Salin, "Spectrophotometric Determination of Aqueous Sulfide on a Pneumatically Enhanced Centrifugal Microfluidic Platform" Analytical Chemistry, 2012, 84 (22), pp. 10038-10043.

A. LaCroix-Fralish, J. Clare, C. D. Skinner and E. D. Salin, "A centrifugal microanalysis system for the determination of nitrite and hexavalent chromium" Talanta, 2009, 80, pp. 670-675.

J. P. Lafleur, A. A. Rackov, S. McAuley and E. D. Salin, "Miniaturised centrifugal solid phase extraction platforms for in-field sampling, pre-concentration and spectrometric detection of organic pollutants in aqueous samples" Talanta, 2010, 81, pp. 722-726.

Y. Xi, E. J. Templeton and E. D. Salin, " Rapid simultaneous determination of nitrate and nitrite on a centrifugal microfluidic device" Talanta, 2010, 82, pp. 1612-1615.

B. Bao, L. Melo, B. Davies, H. Fadaei, D. Sinton and P. Wild, "Detecting Supercritical CO2 in Brine at Sequestration Pressure with an Optical Fiber Sensor" Environmental Science and Technology, 2013, 47, pp. 306-313.

H. Fadaei, J. M. Shaw and D. Sinton, "Bitumen-Touene Mutual Diffusion Coefficients Using Microfluidics" Energy and Fuels, 2013, 27, pp. 2042-2048.

A. Sell, H. Fadaei, M. Kim and D. Sinton, "Measurement of CO2 Diffusivity for Carbon Sequestration: A Microfluidic Approach for Reservoir-Specific Analysis" Environmental Science and Technology, 2013, 47, pp. 71-78.

R. A. Potyrailo, W. G. Morris, A. M. Leach, T. M. Sivavec, M. B. Wisnudel and S. Boyette, "Analog Signal Acquisition from Computer Optical Disk Drives for Quantitative Chemical Sensing" Analytical Chemistry, 2006, 78, pp. 5893-5899.

M. J. Madou and G. J. Kellogg, The LabCD™: A centrifuge-based microfluidic platform for diagnostics, 1998. (14 pages).

M. Madou, J. Zoval, G. Jia, H. Kido, J. Kim and N. Kim, "Lab on a CD" Annual Review of Biomedical Engineering, 2006, 8, pp. 601-628.

J. P. Lafleur and E. D. Salin, "Pre-concentration of trace metals on centrifugal microfluidic discs with direct determination by laser ablation inductively coupled plasma mass spectrometry" Journal of Analytical Atomic Spectrometry, 2009, 24, pp. 1511-1516.

Y. Xi, D. A. Duford and E. D. Salin, "Automated liquid-solid extraction of pyrene from soil on centrifugal microfluidic devices" Talanta, 2010, 82, pp. 1072-1078.

R. N. Sah and P. H. Brown, "Boron Determination—A Review of Analytical Methods" Microchemical Journal, 1997, 56, pp. 285-304.

D. L. Callicoat, "Carminic Add Procedure for Determination of Baron" Analytical Chemistry, 1959, 31, pp. 1434-1437.

Rogel, E., Ovalles, C. and Moir, M., "Asphaltene Stability in Crude Oils and Petroleum Materials by Solubility Profile Analysis," Energy & Fuels, vol. 24(8), 2010, pp. 4369-4374.

Kuo Ju-Nan et al., "Decanting and mixing of supematant human blood plasma on centrifugal microfluidic platform", Microsystem Technologies, Berlin, DE, vol. 22, No. 4, Feb. 8, 2015, pp. 861-869.

Extended Search report issued in the related EP Application 17155890.1, dated Jun. 21, 2017 (11 pages).

D7061—Standard Test Method for Measuring n-Heptane Induced Phase Separation of Asphaltene-Containing Heavy Fuel Oils as

(56) References Cited

OTHER PUBLICATIONS

Separability No. By an Optical Scanning Device, published by the American Society for Testing and Materials (ASTM) (7 pages).

* cited by examiner

CENTRIFUGAL PLATFORM AND DEVICE FOR RAPID ANALYSIS OF OILFIELD FLUIDS

BACKGROUND

Field

The present application relates to test methods, apparatus, and systems for evaluating the effectiveness of organic and inorganic scale inhibitors.

Related Art

Inorganic and organic scale inhibitors (also commonly referred to as dispersants) can be used for flow assurance during the production, transportation, and processing of petroleum reservoir fluids. For example, asphaltene deposition (a type of organic scaling) is an infrequent, but severe impediment during production, transportation, and processing of reservoir fluids. Unexpected precipitation and the subsequent potential for deposition of asphaltene aggregates can cause reservoir impairment, plugging of wells and flowlines, equipment fouling issues, and processing challenges for facilities. The costs associated with the precipitation and deposition of asphaltenes from reservoir fluids during production, transportation, sample handling, and processing of reservoir fluids have been estimated to be on the order of billions of dollars worldwide as described in Rogel, E., Ovalles, C. and Moir, M., "Asphaltene Stability in Crude Oils and Petroleum Materials by Solubility Profile Analysis," *Energy & Fuels*, Vol. 24(8), 2010, pp. 4369-4374.

Since mechanisms of aggregation and deposition are not completely understood, prediction, prevention, and remediation techniques may be difficult to implement. One approach to minimize the possibility for asphaltene deposition is to add one or more asphaltene inhibitors to the reservoir fluid. The asphaltene inhibitor(s) act to slow the formation of asphaltene aggregates; thereby keeping asphaltenes suspended in solution. Since the aggregation behavior of asphaltenes is challenging to predict, the selection of a suitable asphaltene inhibitor that is effective for a particular reservoir fluid is often achieved through an empirical screening process, where a pre-defined library of dispersants are applied to the crude oil sample and evaluated for effectiveness by the addition of a precipitant that induces flocculation. A "good" asphaltene inhibitor will keep asphaltenes suspended and a "poor" asphaltene inhibitor will show precipitation and sedimentation. This process is commonly known as the Asphaltene Dispersion Test (ADT). The optimal solution may be a combination of several asphaltene inhibitors, which are typically in the 50-1000 ppm range. Determining a good combination is often a time consuming process that must be completed for individual oil samples because the asphaltenes vary from one oilfield to another.

One established approach for screening asphaltene inhibitors is published by the American Society for Testing and Materials (ASTM) as standard D7061, "Standard Test Method for Measuring n-Heptane Induced Phase Separation of Asphaltene-Containing Heavy Fuel Oils as Separability Number by an Optical Scanning Device". This method evaluates aggregation and sedimentation of asphaltenes by vertically profiling a sample vial over time using optical transmission measurements. The test is used in conjunction with a commercially available device called the Turbiscan™ LAB stability analyzer, available from Formulaction SA of L'Union, France. A precipitant like n-heptane is added to a sample of crude oil plus dispersant and an optical detection system measures the transmitted and back-scattered light. Vertical scans are performed, in which a motorized stage moves the optical system along the length of the vial in 40 micron increments.

Using the traditional ASTM D7061 method, asphaltene will form and move down the vial under the influence of gravity, which results in significant waiting time for obtaining the results of the testing. For example, after a prescribed time, typically 30 minutes, a good inhibitor will slow down asphaltene sedimentation whereas a poor inhibitor will not. Using this process, batches of asphaltene dispersants are screened and appropriate concentrations selected. The serial nature of the Turbiscan™ analysis makes finding a suitable inhibitor a time consuming task.

Another test protocol for testing inorganic scale inhibitors is NACE TM 0374-2001 and NACE TM 0197-97 or their latest iteration. These protocols require that the fluid to be tested (e.g. seawater) is mixed with a scale inhibitor in a glass jar, which is then placed into a temperature-controlled chamber/bath. Then, after waiting for an amount of time which is representative or the inhibitor exposure time, the results of the reaction are checked either visually (by absorption, scattering, cloudiness, precipitation) or quantitatively (by subsampling from the test jar and using the appropriate tool for the scale of interest).

BRIEF SUMMARY

According to a first aspect, a parallel asphaltene dispersion test (ADT) methodology is provided in which centrifugal separation is used (as a substitute for conventional gravimetric sedimentation in the traditional ASTM D7061 method). A stationary optical system is provided, which can include a light source and a charge-coupled device (CCD) camera that are configured to scan one or more chambers of a rotatable disc corresponding to areas in which asphaltenes can precipitate. The method includes introducing an oil sample to a sample reservoir on the disc, introducing a precipitant to a precipitant reservoir on the disc, introducing an asphaltene inhibitor to an inhibitor reservoir on the disc and/or a solvent to a solvent reservoir on the disc, and rotating the disc to generate centrifugal force to cause the sample, precipitant, solvent, and inhibitor to travel radially outward toward an analysis chamber where the asphaltenes in the oil sample may precipitate out of the oil sample and settle radially outwardly under the influence of the centrifugal force.

The flow of fluids on the disc is controllable based at least in part on the rotational speed of the disc. As a result, it is possible to meter out various ratios of solvent, inhibitor, oil, and precipitant for testing by altering the speed of the disc.

Owing to the features of the test apparatus and the test method described herein, operations such as dilution, mixing, precipitation, and asphaltene separation can be performed on a single portable device, using small quantities of reagents. In addition, when compared to the traditional ASTM D7061 method, which relies on the time consuming gravimetric settling of asphaltenes, the method described herein utilizes centrifugal forces that increase the speed of asphaltene settling, thereby reducing testing times as compared to testing times for the traditional ASTM D7061 method.

DETAILED DESCRIPTION

Illustrative embodiments of the disclosed subject matter of the application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

As used herein, the term "microfluidics" or "microfluidic" refers to a device, apparatus, or system that deals with the behavior, precise control, and manipulation of fluids that are geometrically constrained to a small, typically sub-millimeter, scale. The device, apparatus, or system can employ small, typically sub-millimeter, scale channels that are etched into planar substrates, such as glass, where networks of these embedded channels transport the sample from one operation to the next. The manipulation of small volumes of fluid enables precise control of reagents and seamless automation of several consecutive steps.

The subject matter of the disclosure relates to the evaluation of asphaltene inhibitors using a centrifugal microfluidic testing apparatus and system. Specifically, this disclosure presents a rapid and automated method for screening asphaltene inhibitors using microfluidic technology.

Figure 1:
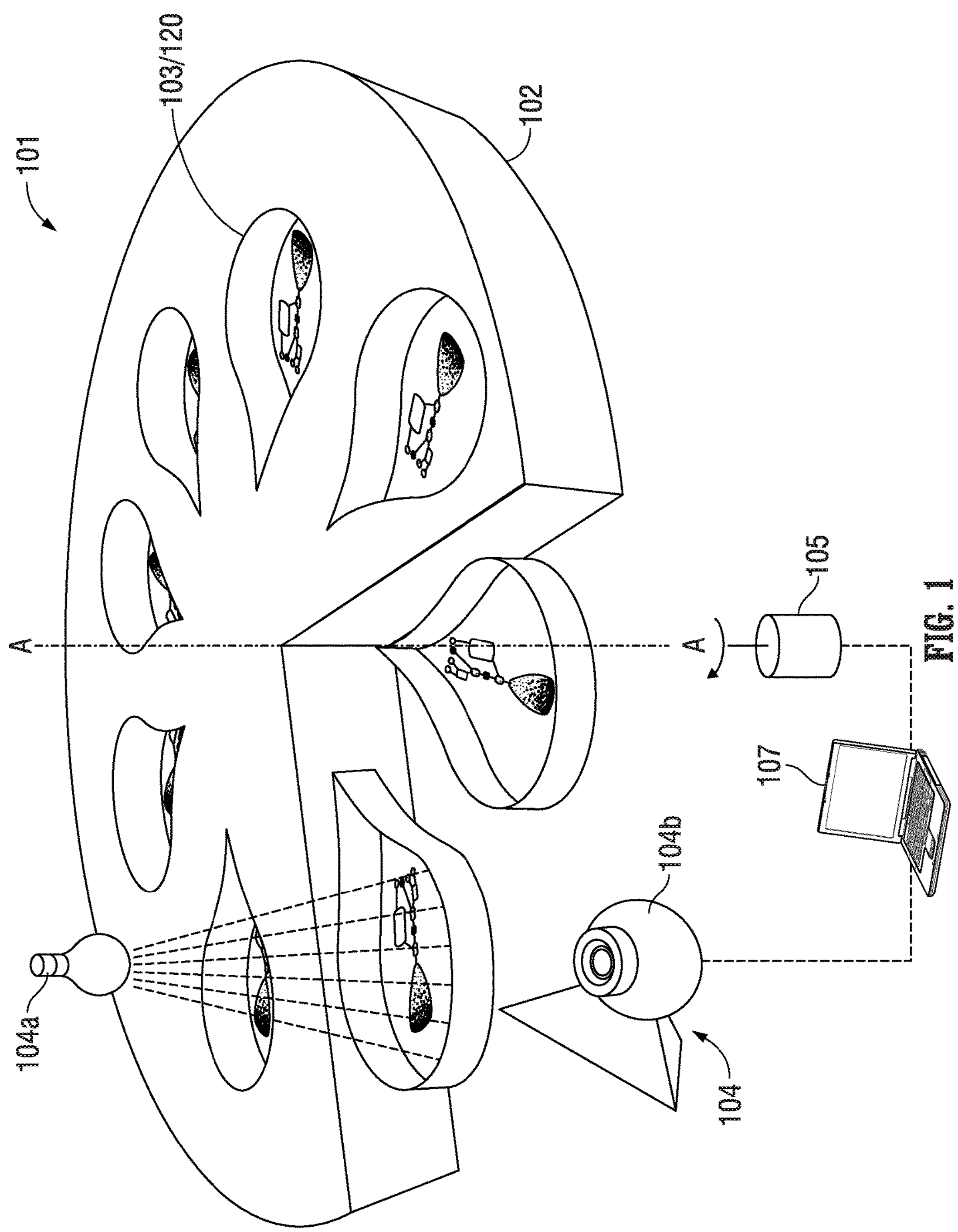
FIG. 1 is a schematic view of a parallel asphaltene dispersion test apparatus.

FIG. 1 depicts an illustrative embodiment of a system 101 for automated fluid analysis of an oil sample. The system 101 includes a disc 102 with multiple microfluidic devices 103 arranged circumferentially about the disc 102. The details of the construction of each microfluidic device 103 will be described in greater detail below with reference to FIG. 2. The microfluidic devices 103 may be integral with the disc 102 or may be separate pieces that are fixed to the disc 102. The disc 102 is constructed to spin as a platter in a clockwise and/or counter-clockwise direction about an axis labeled A-A.

The system 101 also includes a motor 105 coupled to the disc 102. The motor 105 is constructed to regulate the speed, acceleration, and direction of the rotation of the disc 102 about the axis A-A. The motor 105 may be an electric motor operating on DC or AC power.

The system 101 also includes an optical detection system 104 for measuring the optical absorbance of fluid at an analysis chamber 120 that is part of the microfluidic device 103 as the analysis chamber 120 rotates passed the optical detection system 104. The optical detection system 104 can include a light source 104*a* located on one side of the disc 102 and a CCD detector (or camera) 104*b* on the other side of the disc 102 so that the CCD captures an image of the light transmitted through the analysis chamber 120 along the lengthwise dimension of the analysis chamber 120 of the microfluidic device 103. Note that the optical detection system 104 is fixed in position and does not rotate with the disc 102. Instead of a moving optical system as is currently implemented on commercially available scanners like the Turbiscan™ LAB stability analyzer, the disc 102 is rotated so that the analysis chamber 120 of the microfluidic device 103 is passed over the fixed imaging area of the optical detection system 104. In another embodiment, the optical detection system 104 may include a spectrophotometer to measure the absorbance or fluorescence over the lengthwise dimension of the analysis chamber 120 of the rotating microfluidic device 103. In yet another embodiment, the optical detection system 104 may include a light scattering optical system for measuring asphaltene precipitation onsets and also the degree of precipitation.

The system 101 can also include a computer processing system 107 that can be programmed with suitable control logic that interfaces to the motor 105 and the optical detection system 104 via wired or wireless signal paths therebetween. As used herein, the computer processing system 107 may be embodied as at least one controller (e.g., microcontrollers) and/or at least one general purpose computer configured (i.e., programmed) to execute specific control logic, as described in greater detail hereinbelow. The control logic of the computer processing system 107 (which can be embodied in software that is loaded from persistent memory and executed in the computing platform of the computer processing system 107) is configured to control the different parts of the system 101 to carry out an automated sequence of operations (workflow) that characterizes the dispersion of an oil sample mixed with an asphaltene inhibitor. The control logic can be configured by a testing script, which is input into and executed by the computer processing system 107 to perform automatic control operations as specified by the testing script. For example, the control logic may set rotational speed and direction of the disc 102 according to a rotational test protocol so that fluids in the microfluidic device 103 can be mixed in a predefined manner. The computer processing system 107 can include a graphical user interface that allows a user to specify the sequence of automatic control operations and/or the parameters (such as flow rates, temperatures, etc.) for such automatic control operations.

An embodiment of the microfluidic device 103 will now be described with reference to FIG. 2. The microfluidic device 103 may be formed from a substrate 106, which may be made of glass. The substrate 106 may be mountable to the disc 102 as a separate piece or may be integrally formed with the disc 102. The microfluidic device 103 defines various microfluidic chambers and passageways interconnecting the chambers, as will be described below. The substrate 106 may be a temperature-controlled region (e.g., resistive heaters, oven, cooling bath, etc.) that may be used to control the temperature at various locations on the microfluidic device 103, including the various microfluidic chambers and passageways. The temperature control may be used to test for the presence of fines and waxes in an oil sample, as will be described in greater detail below. Such microfluidic chambers and passageways may be machined, etched, or otherwise formed in the microfluidic device 103 as will be appreciated by those of ordinary skill in the art. Fluids move radially outward between the chambers and through the passageways of the microfluidic device 103 as facilitated by the centrifugal and/or capillary forces resulting from rotation of the microfluidic device 103 on the disc 102 driven by the motor 105 about the axis A-A.

Figure 2:
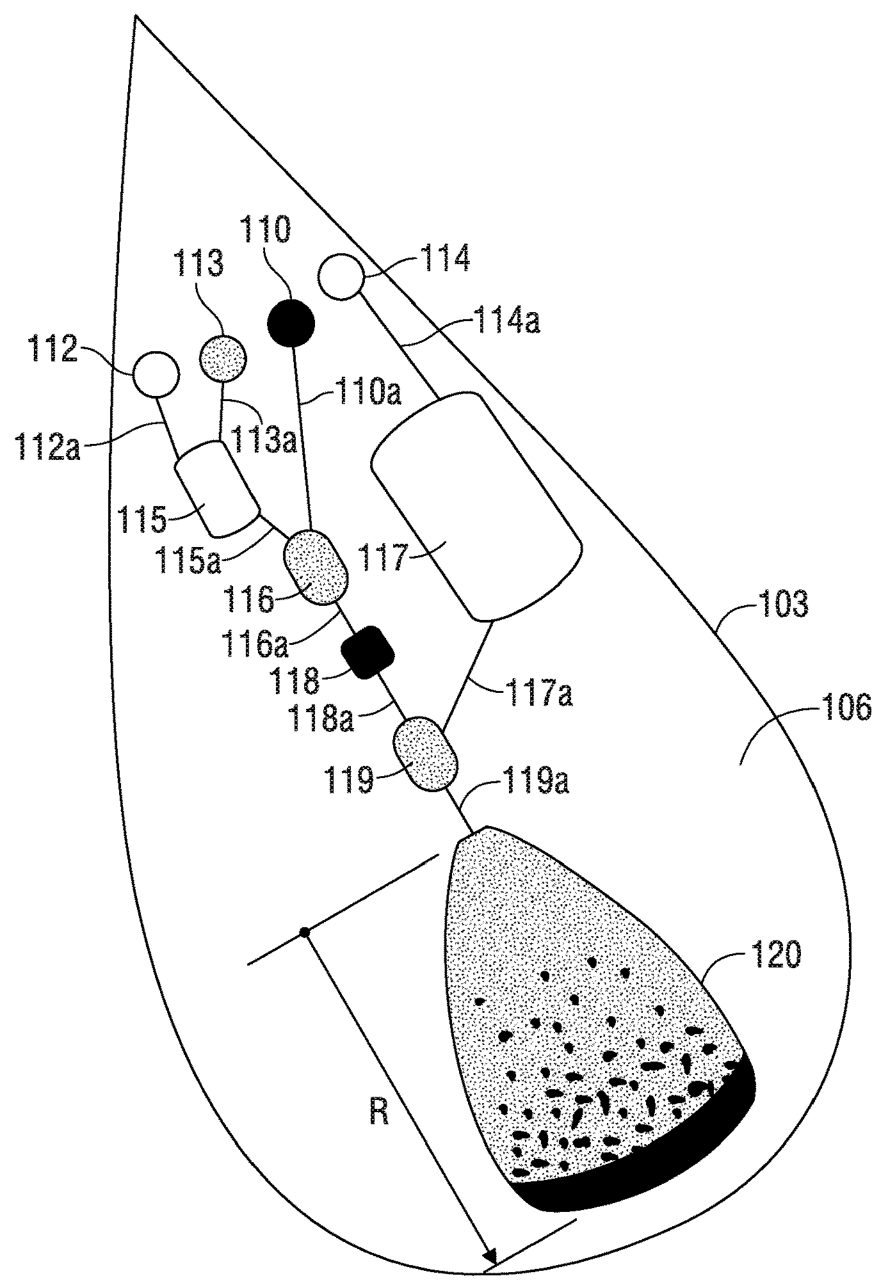
FIG. 2 is a schematic view of a microfluidic device of the apparatus of FIG. 1.

In the embodiment shown in FIG. 2, the microfluidic device 103 has an oil sample reservoir 110 located near the center (axis A-A) of the disc 102. The oil sample reservoir 110 holds an oil sample. The oil sample can include lighter (more volatile) molecular weight components as well as heavy (less volatile) molecular weight components such as heavy oil and bitumen. The oil sample may be manually introduced into the oil sample reservoir 110, such as with a pipette or syringe. Alternatively, the oil sample may be automatically introduced into the oil sample reservoir 110, such as with a syringe pump, which may be electrically operated. In one embodiment the computer processing system 107 may be programmed with suitable control logic that interfaces to such an electrically operated syringe pump via wired or wireless signal paths therebetween to control operation of the syringe pump.

The system 101 also has a solvent reservoir 112 located near the center (axis A-A) of disc 102. The solvent reservoir 112 holds a solvent, which can dissolve asphaltene solids when the solvent is present in the oil sample. The solvent can be toluene, dichloromethane (DCM), xylenes, benzene, methyl naphthalene, cyclohexane, tetrahydrofuran (THF), chloroform, trichloroethylene, tetrachloroethylene, carbon tetrachloride, carbon disulfide, and other suitable solvents. The solvent may be manually introduced into the solvent reservoir 112, such as with a pipette or syringe. Alternatively, the solvent may be automatically introduced into the solvent reservoir 112, such as with a syringe pump, which may be electrically operated. In one embodiment the computer processing system 107 may be programmed with suitable control logic that interfaces to such an electrically operated syringe pump via wired or wireless signal paths therebetween to control operation of the syringe pump.

The microfluidic device 103 also has an inhibitor reservoir 113 located near the center (axis A-A) of disc 102. The inhibitor reservoir 113 is configured to hold one or more asphaltene inhibitor(s). The asphaltene inhibitor(s) is an additive that can be blended with the oil sample to identify an appropriate additive and additive concentration that retards or prevents the undesirable reaction that forms asphaltene aggregates when the oil sample is mixed with a precipitant at concentrations that result in the formation of asphaltene aggregates. Such analysis may be useful to mitigate problems that can arise from asphaltene precipitation of the particular oil during its production and/or transport. The asphaltene inhibitor(s) may be manually introduced into the inhibitor reservoir 113, such as with a pipette or syringe. Alternatively, the asphaltene inhibitor(s) may be automatically introduced into the inhibitor reservoir 113, such as with a syringe pump, which may be electrically operated. In one embodiment the computer processing system 107 may be programmed with suitable control logic that interfaces to such an electrically operated syringe pump via wired or wireless signal paths therebetween to control operation of the syringe pump.

The microfluidic device 103 also has a precipitant reservoir 114 located near the center (axis A-A) of disc 102. The precipitant reservoir 114 is configured to hold a precipitant that can cause asphaltenes to precipitate from the oil sample when the precipitant is mixed with the oil at sufficient concentrations. The precipitant can be an n-alkane (such as n-heptane ($C_7H_{16}$), n-hexane ($C_6H_{14}$), or n-pentane ($C_5H_{12}$)) or other solvents, such as petroleum ether, ethyl acetate, alcohols or any other solvent, which can cause asphaltene precipitation due to a limited solubility. The precipitant may be manually introduced into the precipitant reservoir 114, such as with a pipette or syringe. Alternatively, the precipitant may be automatically introduced into the precipitant reservoir 114, such as with a syringe pump, which may be electrically operated. In one embodiment the computer processing system 107 may be programmed with suitable control logic that interfaces to such an electrically operated syringe pump via wired or wireless signal paths therebetween to control operation of the syringe pump.

The solvent reservoir 112 and the inhibitor reservoir 113 are both fluidly coupled to a dilution chamber 115 that is located radially outward with respect to the reservoirs 112, 113. A solvent channel **112*a* fluidly couples the solvent reservoir 112 to the dilution chamber 115. An inhibitor channel 113*a* fluidly couples the inhibitor reservoir 113 to the dilution chamber 115. The dimensions of the solvent channel 112*a* and the inhibitor channel 113*a* are configured so that when the microfluidic device 103 is rotated at a predetermined speed, metered amounts of solvent and/or inhibitor will be displaced from the respective reservoirs 112, 113 and into the dilution chamber 115 under the influence of centrifugal force caused by the rotation of the microfluidic device 103 with the disc 102. It will be appreciated that the movement of the solvent and the inhibitor will be a function at least of the viscosity of the fluid, the geometry and dimensions of the channels 112*a*, 113*a*, and the rotational speed of the microfluidic device 103. The dilution chamber 115 can provide a space for the solvent and inhibitor to be metered out and/or mixed. The dilution chamber 115 can be configured such that the inhibitor is diluted with the solvent in an automated way using only the microfluidic device (i.e., "on-chip"), which avoids manually diluting the inhibitor off of the microfluidic device 103 (i.e., "off-chip") and loading the diluted inhibitor onto the microfluidic device 103** in a separate operation. The solvent/inhibitor/oil ratio may be predetermined based on the standard or test protocol employed. In one example, the inhibitor is mixed with the solvent and the oil so that the desired amount of inhibitor is in a range from about 50 ppm to 1000 ppm. It may be desirable to minimize the dosages of solvent and inhibitor to keep cost low during implementation in the field, while ensuring stabilization of asphaltenes. Therefore, when the dosages of solvent and inhibitor are minimized, the crude oil comprises the majority of the mixture that is mixed with the precipitant.

The oil sample reservoir 110 and the dilution chamber 115 are both fluidly coupled to a first mixing chamber 116 that is located radially outward with respect to the oil sample reservoir 110 and dilution chamber 115. Channel **110*a* fluidly couples the oil sample reservoir 110 to the first mixing chamber 116. Channel 115*a* fluidly couples the dilution chamber 115 to the first mixing chamber 116. The first mixing chamber 116 provides microfluidic mixing of the fluids from the dilution chamber 115 and oil displaced from the oil sample reservoir 110. Specifically, metered amounts of the fluid in the dilution chamber 115 and oil will be displaced from their respective dilution chamber 115 and oil sample reservoir 110 and into the first mixing chamber 116 under the influence of centrifugal force caused by the rotation of the microfluidic device 103 with the disc 102**.

The precipitant reservoir 114 is fluidly coupled by channel 114*a* to a first volumetric gate 117 that is located radially outward with respect to the precipitant reservoir 114. Precipitant can be displaced from the precipitant reservoir 114 to the first volumetric gate 117 under the influence of centrifugal force when the microfluidic device 103 rotates with the disc 102. The outlet of the first volumetric gate 117 can optionally be selectively opened or closed, such as by means of a flapper valve, to permit fluid therein to move radially outwardly from the first volumetric gate 117. The opening of the outlet of the first volumetric gate 117 can be controlled so that the fluids displaced from the first volumetric gate 117 can be accurately metered out from the first volumetric gate 117.

The first mixing chamber 116 is fluidly coupled to a second volumetric gate 118 that is located radially outward with respect to the first mixing chamber 116. Channel 116*a* fluidly couples the first mixing chamber 116 to the second volumetric gate 118. Fluid can be displaced from the first mixing chamber 116 to the second volumetric gate 118 under the influence of centrifugal force when the microfluidic device 103 rotates with the disc 102. The outlet of the second volumetric gate 118 can optionally be selectively opened or closed, such as by means of a flapper valve, to permit fluid therein to move radially outwardly from the second volumetric gate 118. The opening of the outlet of the second volumetric gate 118 can be controlled so that the fluids displaced from the second volumetric gate 118 can be accurately metered out from the second volumetric gate 118 through channel 118*a*.

The outlets of the first and second volumetric gates 117, 118 are both fluidly coupled to a second mixing chamber 119 that is located radially outward with respect to the volumetric gates 117, 118. Channel 117*a* fluidly couples the outlet of the first volumetric gate 117 to the second mixing chamber 119. Channel 118*a* fluidly couples the outlet of the second volumetric gate 118 to the second mixing chamber 119. The second mixing chamber 119 provides microfluidic mixing of the fluids from the volumetric gates 117, 118. Specifically, metered amounts of the precipitant can be dispensed into the second mixing chamber 119 by operation of the first volumetric gate 117 and metered amounts of the fluid from the first mixing chamber 116 can be displaced into the second mixing chamber 119 by operation of the second volumetric gate 118 so that microfluidic mixing of the precipitant and the oil and solvent/inhibitor can take place in the second mixing chamber 119 under the influence of centrifugal force caused by the rotation of the microfluidic device 103 with the disc 102.

The first and second volumetric gates 117, 118 are chambers with accurately known volumes that may have built-in valving mechanisms. The first and second volumetric gates 117, 118 may accurately dispense fluid from their respective chambers using such valving mechanisms so that a desired dilution/mixing ratio of fluids issuing from the first and second volumetric gates is achieved in the second mixing chamber 119. The first and second volumetric gates 117, 118 can be activated by different means.

For example, one or both of the volumetric gates 117, 118 can be configured with valves at an exit port on a radially outward end of the respective gates 117, 118. Such valves can be configured to open above a predetermined rotational speed of the device 103 and to remain closed when the rotational speed of the microfluidic device 103 is below the predetermined rotational speed. An example of a speed responsive valve of a volumetric gate may be a spring-loaded valve that is constructed so that at a rotational speed below a predetermined threshold, the valve will be subject to a centrifugal force below the spring load of the valve which does not open the valve so that that fluid entering the volumetric gate from an inlet port will tend to fill the chamber of the volumetric gate. At a rotational speed above a threshold, the spring-loaded valve may be subject to a centrifugal force above the spring load of the valve, which causes the valve to open at the exit port so that fluid in the volumetric gate will tend to drain from the volumetric gate radially outwardly.

In another embodiment, the volumetric gates 117, 118 may not include any valve mechanism. Instead, all of the fluids to be mixed may be accurately dosed (e.g., using an accurate pipette) and dispensed into the reservoirs 110, 112, 113, 114 before the microfluidic device 103 is rotated. Then, the microfluidic device 103 is rotated until all of the closed fluids are mixed so that the mixture includes all of the dosed amounts so that the fluid concentrations are known.

The outlet of the second mixing chamber 119 is fluidly coupled to an analysis chamber 120 that is located radially outward with respect to the second mixing chamber 119. Channel 119*a* fluidly couples the outlet of the second mixing chamber 119 to the analysis chamber 120. Mixed fluids in the second mixing chamber 119 may be displaced radially outwardly from the second mixing chamber 119 into the analysis chamber 120 under the influence of centrifugal force caused by the rotation of the microfluidic device 103 with the disc 102.

The direction and speed of rotation of the microfluidic device 103 can be controlled to control the radial flow of fluid between chambers on the device 103. The rotation speed and direction can be controlled according to a protocol based on the configuration of the microfluidic device 103 (e.g., chamber geometry, channel sizes, etc.).

In one embodiment, the analysis chamber 120 can be constructed as an integrated microfluidic optical absorbance flow cell. Examples of such a flow cell are described in Sieben, V. J., et al., "Microfluidic colourimetric chemical analysis system: Application to nitrite detection," *Analytical Methods* 2(5), 2010, pp. 484-491; and Hwang, H. et al., "Lab-on-a-Disc for Simultaneous Determination of Nutrients in Water," *Analytical Chemistry* 85, 2013, pp. 2954-2960, herein incorporated by reference in their entireties.

During operation involving the rotation of the microfluidic device 103 with the disc 102, the mixing of the precipitant and the oil sample in the second mixing chamber 119 can cause asphaltenes to precipitate from the mixture. Such precipitated asphaltenes are typically referred to as asphaltene floccules or asphaltene flocks. The asphaltene flocks are carried as a suspension in the liquid phase of the mixture into the analysis chamber 120. The liquid phase of the mixture includes the maltenes of the oil sample, which are the lower molecular weight components of the oil sample that remain after removing the precipitated asphaltenes. The maltenes are also soluble in the precipitant. The centrifugal force caused by the rotation of the microfluidic device 103 with the disc 102 causes the precipitated asphaltene flock, if present, to settle rapidly near the distal end of the analysis chamber 120. When the mixed sample is in the analysis chamber 120, the rotational speed of the microfluidic device 103 may be set by a user to test for sedimentation, i.e., of asphaltene flocculates. For example, the rotational speed for sedimentation may be set by a user as a function of desired centrifugal force, i.e., for a desired equivalent of "g". Centrifugal force can range from 1 g to 20,000 g, but will typically range from 1 g to 10 g for the separation of flocculates having a size on an order of a micron. More centrifugal force will cause sedimentation/collection of smaller asphaltene particles, permitting more stringent control over the screening for effective inhibitors.

Figure 3:
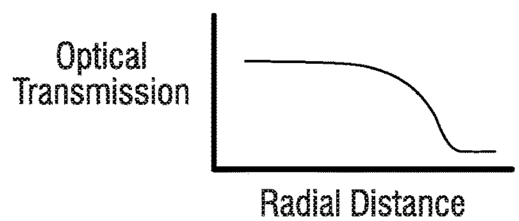
FIG. 3 is a representative graph showing optical transmission versus radial distance in an analysis chamber of the microfluidic device of FIG. 2.

The analysis chamber 120 may be constructed as an optical flow cell, which can be scanned by the optical detection system 104, which, as noted above, may include a spectrophotometer in communication with the computer processing system 107. The spectrophotometer can be operated to measure optical absorbance over the lengthwise dimension R of the analysis chamber 120 of the rotating microfluidic device 103. Such measurements can be used to generate a graph of optical transmission through the analysis chamber 120 as a function of radial distance R of the analysis chamber 120. An example of such graph is shown in FIG. 3.

The transmittance of light through crude oil is dependent on the concentration of asphaltenes, since asphaltenes strongly absorb light. As such, the change in transmittance over time along the length R of the analysis chamber 120 can be used to monitor asphaltene stability by determining changes over time in asphaltene content in the different regions or entire length R of the analysis chamber 120.

Once the oil/inhibitor/solvent mixture is introduced into the analysis chamber 120, optical properties (such as light transmission) of the liquid phase (maltenes) and solid phase (asphaltenes) in the analysis chamber 120 can be monitored along the entire distance R during the period of rotation of the microfluidic device 103. Such properties can be evaluated to detect changes in the mixture's solids concentration (asphaltenes concentration) at various radial positions in the chamber 120. More specifically, as the dispersed asphaltene flock particles scatter light, light transmission will increase in areas that are losing solids (asphaltenes) and decrease (if not already opaque) in areas that are gaining solids (asphaltenes).

Figure 4E:
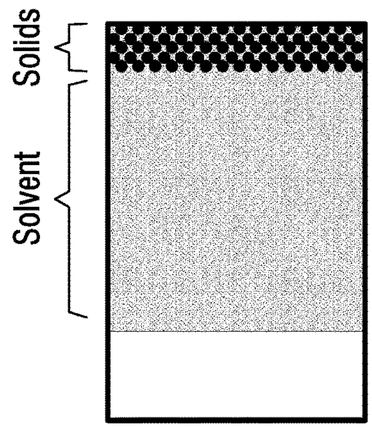
FIGS. 4A to 4F show a schematic representation of solids in a mixture of oil/inhibitor/precipitant in an analysis chamber of a microfluidic device (upper image) and light transmission as functions of radial position in the analysis chamber (lower image) at an initial time (FIGS. 4A and 4B), intermediate times (FIGS. 4C and 4D), and at the end of testing (FIGS. 4E and 4F).
Figure 4F:
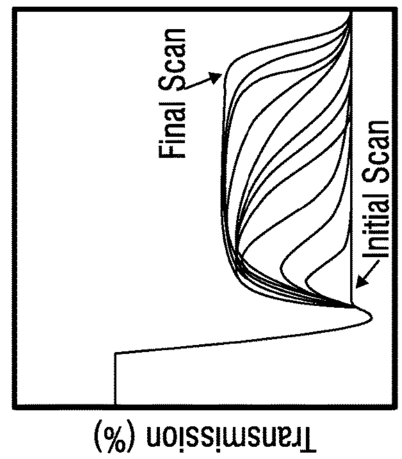
Figure 4C:
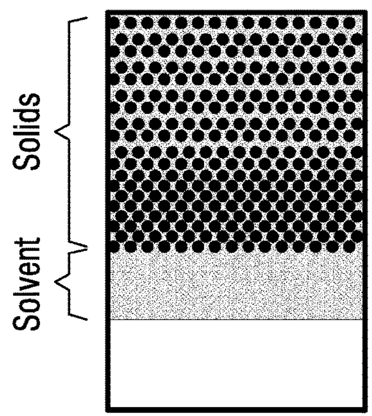
Figure 4D:
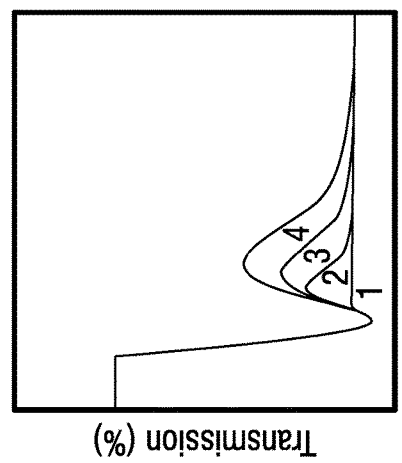
Figure 4A:
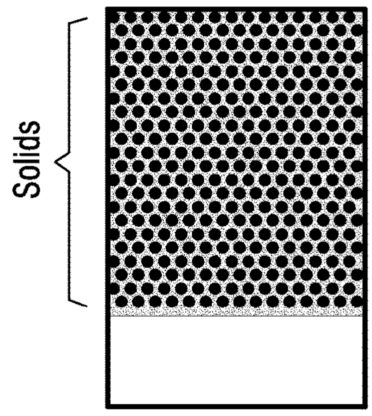
Figure 4B:
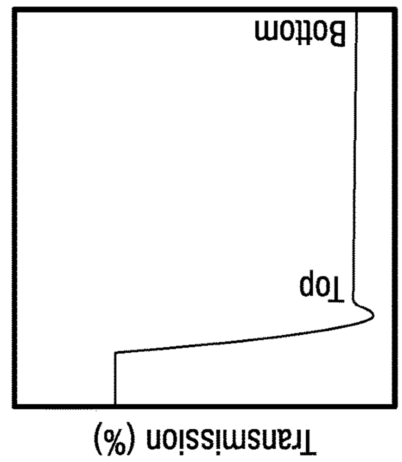

FIG. 4A shows that upon initial introduction of the oil/inhibitor/solvent mixture into the analysis chamber 120, a relatively evenly dispersed mixture of solids exists along substantially the entire length R of the analysis chamber 120. FIG. 4B shows an initial trace after the oil/inhibitor/precipitant mixture is introduced into the analysis chamber 120. In this case, the light transmission through the analysis chamber 120 is relatively uniform along the entire length R of the analysis chamber 120.

However, as the microfluidic device 103 is rotated further, the dispersion breaks down and asphaltene solids start separating from the oil/solvent/inhibitor mixture and move towards the radially outer portion of the analysis chamber 120. See, e.g., FIG. 4C. As the solids separate, the transmission of light through the analysis chamber 120 increases at the radially inner portions of the analysis chamber. See, e.g., FIG. 4D, traces 2 to 4 showing plots of transmittance through the analysis chamber 120 at different times.

FIG. 4D illustrates that over a certain period of time after initial introduction of the oil/inhibitor/precipitant mixture, light transmission through the analysis chamber 120 at radially inner positions of the analysis chamber 120 increases as asphaltene solids settle radially outwardly over time, i.e., from traces 2 to 4. As the microfluidic device 103 is rotated further, additional asphaltene settling continues radially outwardly, thereby causing light transmission through the analysis chamber 120 to increase progressively over the radially outward direction. At the radially outer end of the analysis chamber 120, the transmission of light decreases when there is an increase of asphaltene solids settling there. See, e.g., FIG. 4E. FIG. 4F shows additional traces 5 to 12 over the analysis chamber 120 that illustrate that the light transmittance has increased almost the entire length R of the analysis chamber 120 with the exception of the radially outer end where the asphaltene solids have collected.

The transmittance data that represents light transmission through the analysis chamber 120 at varying radial positions of the analysis chamber 120 can be used to calculate an instability index, which is a measure of normalized potential for solids flocculation and settling from the oil sample. Specifically, the instability index is a calculation of the change in integral transmission between time 0 and a time t, normalized by the maximum theoretical transmission, resulting in a calculated value from 0 to 1.0. An instability index value of 0 indicates a completely stable sample with no change in the transmittance trace, whereas an instability value of 1 indicates a completely unstable sample with a full change in the transmittance trace occurring.

If asphaltenes are destabilized by the addition of the precipitant, the transmittance trace will behave similar to that illustrated in FIGS. 4B, 4D, and 4F and the destabilized asphaltenes will, over the period of time the microfluidic device 103 is spun, largely settle to the radially outer end of the analysis chamber 120. The greater the amount of asphaltenes destabilized, the larger the magnitude of the transmittance increase. In evaluating asphaltene inhibitors, the inhibitor that can reduce the asphaltene destabilization as evidenced by the lowest instability index (least transmittance change) provides the best inhibition. Thus, tests on different inhibitors or different inhibitor ratios can be performed to evaluate and select inhibitors that are most effective for a specific crude oil sample.

Figure 5:
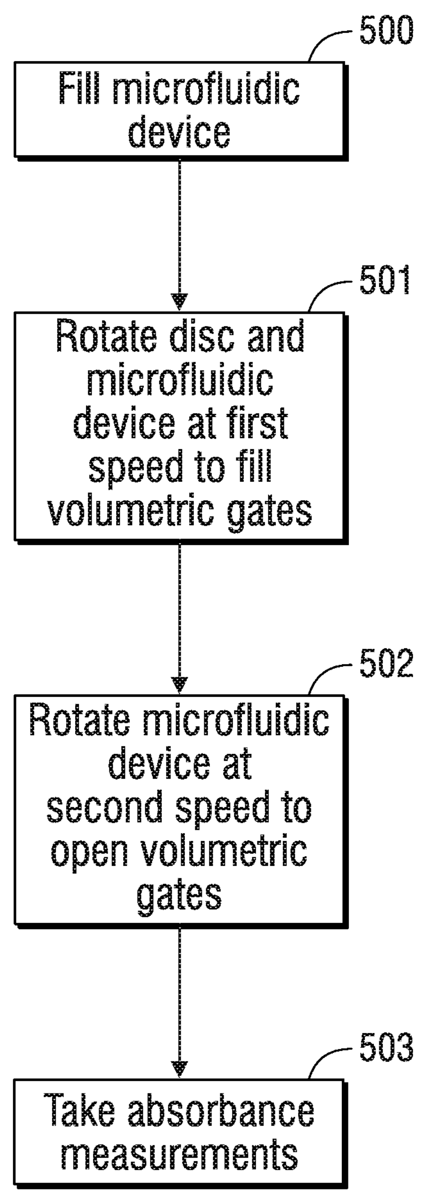
FIG. 5 is a flow chart illustrating a workflow for performing a test using the apparatus of FIG. 1.

FIG. 5 illustrates a workflow for evaluating an asphaltene inhibitor using the system 101 described above. At block 500 one or more of the oil sample reservoir 110, the solvent reservoir 112, the inhibitor reservoir 113, and the precipitant reservoir 114 are filled or dosed, respectively, with sample, solvent, inhibitor, and precipitant.

At block 501 the filled or dosed microfluidic device 103 is rotated at a first rotational speed with the disc 102 so that the solvent and the inhibitor flows radially outward into the dilution chamber 115 and into the first mixing chamber 116, while the oil sample flows radially outward into the first mixing chamber 116 to mix with the solvent and the inhibitor. The mixture formed in the first mixing chamber 116 flows radially outward to the second volumetric gate 118. In parallel with such fluid flow, the precipitant flows radially outward into the first volumetric gate 117. The first rotational speed can be set so that the first and second volumetric gates 117, 118 remain closed in the case that valves actuated at predefined rotational speeds are used.

The dimensions of the channels **112*a*, 113*a*, and 110*a* are configured so that the ratio of solvent to inhibitor to oil can be controlled and the oil sample can be diluted with a predetermined concentration of the solvent. For example, the dimensions of the channels 112*a* and 110*a*** may be configured so that 1000 ppm inhibitor is diluted down to 50 ppm with toluene and then mixed with the oil sample. The diluted inhibitor can then be mixed with precipitant at a desired precipitant-to-oil ratio, such as 40:1, or even 1:1.

At block 501 microfluidic mixing that occurs in the first mixing chamber 116 allows the solvent of the sample/solvent mixture to dissolve most if not all of the asphaltene content of the sample/solvent mixture (if any asphaltene content is present from the oil sample). At least a portion of the fluid in the first mixing chamber 116 flows into the second volumetric gate 118.

At block 502, after the mixture of solvent, inhibitor, and oil sample is loaded into the second volumetric gate 118 and the precipitant is loaded into the first volumetric gate 117, the disc 102 is rotated at a second speed, different from the first speed, to open the first and second volumetric gates 117, 118. When the first and second volumetric gates 117, 118 are opened, the mixture of the solvent, inhibitor, and oil as well as the precipitant flow radially outward to the second mixing chamber 119 for mixing, whereupon the resultant mixture flows radially outward into the analysis chamber 120.

After the oil/precipitant/inhibitor mixture enters the analysis chamber 120, there may be a "waiting time" during which the disc 102 and microfluidic device 103 are not rotated in order to allow for the onset of precipitation of asphaltenes. Such waiting time may be dependent on the sample, the inhibitor, and/or the precipitant, as well as the respective concentrations. Also, the waiting time may be dependent on a predefined test protocol. At the end of any such "waiting time", at block 503, the disc 102 is rotated at or above the second speed so that the analysis chamber 120 passes the detection point of the optical detection system 104, which is located at a fixed position. The optical detection system 104 may measure the optical absorbance of the fluid mixture in the analysis chamber 120 as a function of radial distance in the analysis chamber 120. The computer processing system 107 may output or store one or more graphs, like that shown in FIG. 3 of the optical transmission as a function of radius. The optical absorbance may be measured periodically, such as once per revolution of the disc 102, to determine the effectiveness of the mixed inhibitor, as discussed above.

A comparison of graphs like that in FIG. 3, taken over a period of time, can indicate trends in the asphaltene sedimentation. For example, a good inhibitor will slow down asphaltene sedimentation, whereas a poor inhibitor will not slow down asphaltene sedimentation. By using the method of FIG. 5 batches of asphaltene inhibitors can be screened and appropriate concentrations selected.

The microfluidic devices 103 can be used to conduct various experiments. For example, the microfluidic devices 103 can be used to conduct parallel ADT experiments in which the same inhibitor (i.e., the same chemical) is evaluated at different ratios with the oil/solvent/precipitant mixture. For example, in one experimental setup, a plurality of the microfluidic devices 103 are loaded onto the disc 102 and the amount of the inhibitor filled into the respective inhibitor reservoirs 113 is varied across multiple microfluidic devices 103, while the volumes of precipitant, solvent, and oil in their respective reservoirs is fixed so that the effect of different concentrations on asphaltene dispersion for a specific inhibitor can be evaluated.

Alternatively, the microfluidic devices 103 can be used to conduct parallel ADT experiments in which different inhibitors (i.e., different chemicals) are evaluated at the same ratio with the oil/solvent/precipitant mixture. For example, in another experimental setup, a plurality of microfluidic devices 103 is loaded onto a disc 102 and equal amounts (by volume) of different inhibitors are loaded into each inhibitor reservoir 113 while the volumes of precipitant, solvent, and oil in their respective reservoirs is fixed so that the effect of different inhibitors on asphaltene dispersion can be evaluated. In one example, the relative concentrations between oil, inhibitor, and precipitant are determined by a standard protocol or method employed. For instance ASTM D7601-04 requires at least 97% precipitant (destabilizing solvent) and no more than 2.67% oil. The paper by Jennings et al., "MS New Dead-Crude Oil Asphaltene Inhibitor Test Method", Offshore Technology Conference, May 5, 2014, describes a method that uses from 5-40 volume percent of oil. The standard or test protocol used will be preserved across the range of screened inhibitors.

Typically, as a starting point in evaluating an inhibitor among various inhibitors, the concentration of various inhibitors are kept constant to evaluate the relative ability of the inhibitors in keeping asphaltenes suspended. Then, once a select group of inhibitors are determined as being relatively better at keeping asphaltenes suspended at the tested concentration, the concentrations of those inhibitors may be varied to determine respective optimum concentrations for the selected group of inhibitors. In one example, the inhibitor that provides the best results at the lowest inhibitor concentration is identified as the preferred inhibitor.

As noted above, the substrate 106 of the microfluidic device 103 may be temperature-controlled to regulate the temperature along the fluid pathways of the microfluidic device 103. The temperature may be regulated to test for the presence of fines and waxes in a crude oil sample in accordance with the disclosure of International Patent Application PCT/US2015/037896 entitled "Microfluidic Method for Detection of Fines, Waxes, and Asphaltenes in Oil", the contents of which are incorporated herein by reference. It will be appreciated that for such testing for the presence of fines and waxes, the microfluidic device 103 may be modified to be the same as that of the microfluidic chip 111 of International Patent Application PCT/US2015/037896 with the exception of the pumps described therein. Of course other modifications to microfluidic device 103 may be made to adapt the microfluidic device 103 for use in detecting the presence of fines and waxes in accordance with International Patent Application PCT/US2015/037896, which will be appreciated by those of ordinary skill in the art. In that regard, instead of the pumps described in International Patent Application PCT/US2015/037896, centrifugal force caused by rotation of the disc 102 and the microfluidic device 103 can be used to adjust the pressure of the oil sample through the microfluidic device 103.

A second embodiment of a microfluidic device 603 which can be substituted for microfluidic device 103 of disc 102 will now be described with reference to FIG. 6. The microfluidic device 603 may be formed from a substrate 606, which may be made of glass. The substrate 606 may be mountable to the disc 102 as a separate piece or may be integrally formed with the disc 102. The microfluidic device 603 defines various microfluidic chambers and passageways interconnecting the chambers, as will be described below. The substrate 606 may include a temperature-controlled region (e.g., resistive heaters, oven, cooling bath, etc.) that may be used to control the temperature at various locations on the microfluidic device 603, including the various microfluidic chambers and passageways. The microfluidic chambers and passageways may be machined, etched, or otherwise formed in the microfluidic device 603 as will be appreciated by those of ordinary skill in the art. Fluids move radially outward between the chambers and through the passageways of the microfluidic device 603 as facilitated by the centrifugal and/or capillary forces resulting from rotation of the microfluidic device 603 on the disc 102 driven by the motor 105 about the axis A-A.

Figure 6:
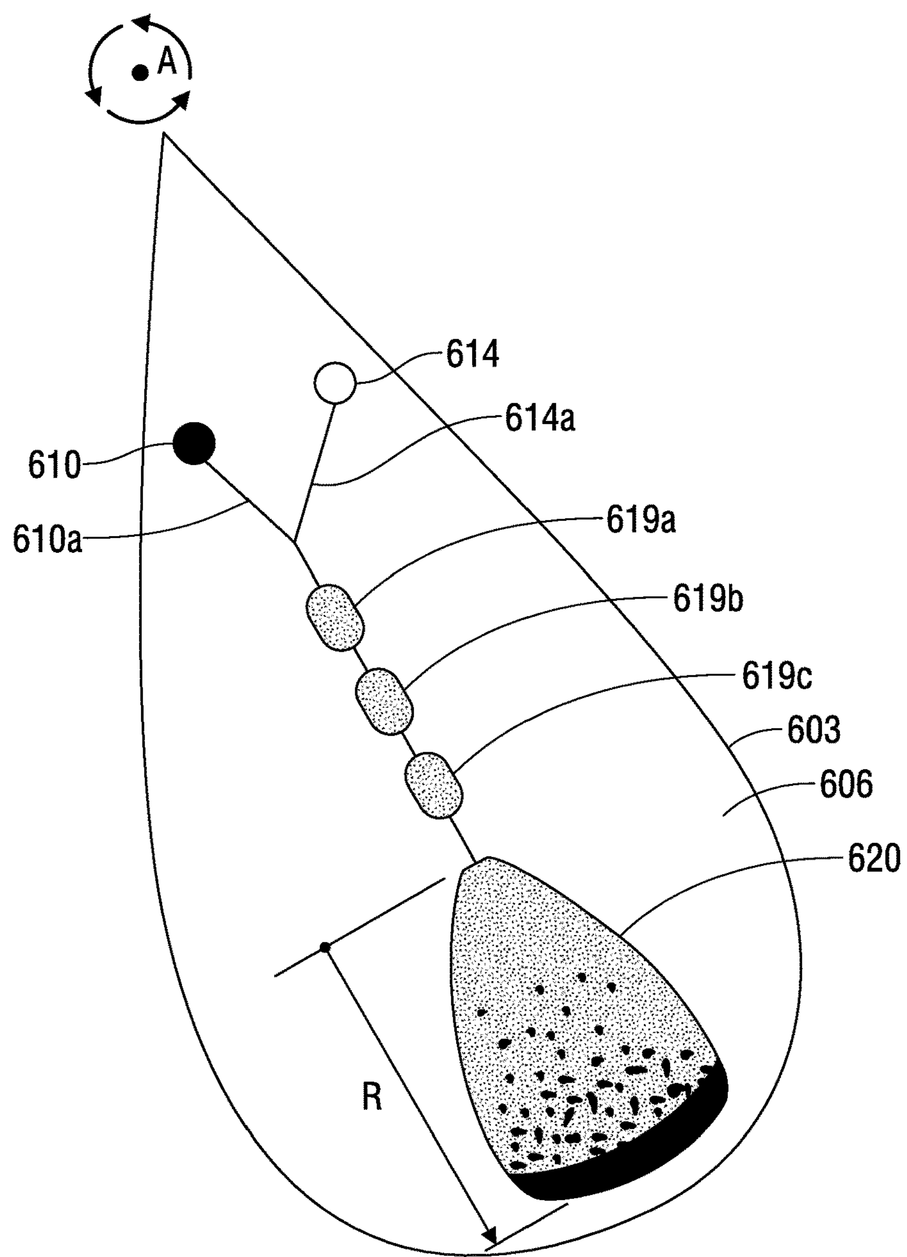
FIG. 6 is a schematic view of a second embodiment of a microfluidic device of the apparatus of FIG. 1.

In the embodiment shown in FIG. 6, the microfluidic device 603 has an oil sample reservoir 610 located near the center (axis A-A) of the disc 102. The oil sample reservoir 610 holds an oil sample that has been premixed with an inhibitor. The oil sample can include lighter (more volatile) molecular weight components as well as heavy (less volatile) molecular weight components such as heavy oil and bitumen. The oil and inhibitor may be manually premixed and introduced into the oil sample reservoir 610, such as with a pipette or syringe.

The microfluidic device 603 also has a precipitant reservoir 614 located near the center (axis A-A) of disc 102. The precipitant reservoir 614 is configured to hold a precipitant that can cause asphaltene to precipitate from the oil sample when the precipitant is mixed with the oil at sufficient concentrations. The precipitant can be an n-alkane (such as n-heptane ($C_7H_{16}$), n-hexane ($C_6H_{14}$), or n-pentane ($C_5H_{12}$)) or other solvents, such as petroleum ether, ethyl acetate, alcohols or any other solvent, which can cause asphaltene precipitation due to a limited solubility. The precipitant may be manually introduced into the precipitant reservoir 614, such as with a pipette or syringe.

The oil sample reservoir 610 and the precipitant reservoir 614 are both fluidly coupled to a first mixing chamber 619*a* that is located radially outward with respect to the oil sample reservoir 610 and the precipitant reservoir 614. Channel 610*a* fluidly couples the oil sample reservoir 610 to the first mixing chamber 619*a*. Channel 614*a* fluidly couples the precipitant reservoir 614 to the first mixing chamber 619*a*. The first mixing chamber 619*a* provides a first micro-mixing stage for microfluidic mixing of the oil, inhibitor, and the precipitant. Specifically, metered amounts of the oil/inhibitor and precipitant will be displaced from their respective reservoirs 610 and 614 into the first mixing chamber 619*a* under the influence of centrifugal force caused by the rotation of the microfluidic device 603 with the disc 102.

The first mixing chamber 619*a* is fluidly coupled to a second mixing chamber 619*b* located radially outward from the first mixing chamber 619*a*. The second mixing chamber 619*b* acts as a second microfluidic mixing stage for the oil/inhibitor/precipitant mixture. Also, the second mixing chamber 619*b* is fluidly coupled to a third mixing chamber 619*c* that is located radially outward from the second mixing chamber 619*b*. The third mixing chamber 619*b* acts as a third microfluidic mixing stage for the oil/inhibitor/precipitant mixture. The third mixing chamber 619*c* is fluidly coupled to an analysis chamber 620 that is located radially outward with respect to the third mixing chamber 619*c*. It will be appreciated that while three mixing chambers are described, fewer or more mixing chambers may be used. The mixed fluids in the third mixing chamber 619*c* may be displaced radially outwardly into the analysis chamber 620 under the influence of centrifugal force caused by the rotation of the microfluidic device 603 with the disc 102. Thereafter, the scanning and analysis of the mixture in the analysis chamber 620 progresses in the same manner described above with reference to FIGS. 4A to 4F.

Figure 8:
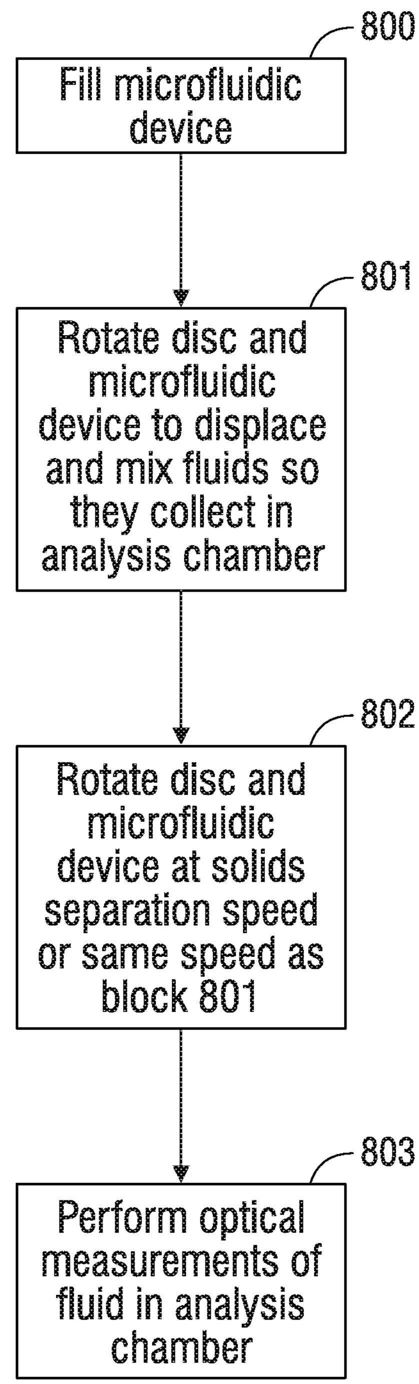
FIG. 8 is a flow chart illustrating another embodiment of a workflow for performing a test using the apparatus of FIG. 1 and the device of FIG. 6.

FIG. 8 illustrates a workflow for evaluating an asphaltene inhibitor using the system 101 described above, but modified to incorporate the microfluidic device 603 instead of microfluidic device 103. At block 800 the oil sample reservoir 610 and the precipitant reservoir 614 are filled or dosed, respectively, with crude oil/inhibitor and precipitant.

At block 801 the filled or dosed microfluidic device 603 is rotated at a first rotational speed with the disc 102 so that the crude oil/inhibitor and the precipitant flow radially outward successively into the first mixing chamber 619*a*, the second mixing chamber 619*b*, and the third mixing chamber 619*c*.

The dimensions of the channels 610*a* and 614*a* are configured so that the ratio of oil/inhibitor to precipitant can be controlled. The inhibitor/oil is then mixed with precipitant at a desired precipitant-to-crude ratio, such as 40:1, or even 1:1.

At block 801 microfluidic mixing that occurs in the mixing chambers 619*a*, 619*b*, and 619*c* allows the oil/inhibitor to mix fully with the precipitant before moving radially outward from the third mixing chamber 619*c*. Also, in block 801, eventually all of the fluid loaded onto the microfluidic device 603 will move from the third mixing chamber 619*c* into the analysis chamber 620.

After the oil/precipitant/inhibitor mixture enters the analysis chamber 620, there may be a "waiting time" during which the disc 102 is not rotated to allow for the onset of precipitation, which may be dependent on the sample, inhibitor, and/or precipitant, as well as the respective concentrations. Also, the waiting time may be dependent on a predefined test protocol. At the end of any such waiting time, at block 802, the disc 102 and microfluidic device 603 are rotated together at a second, solids-separation speed to promote and speed up the separation of asphaltene solids from the crude oil. As the disc 102 and the microfluidic device 603 rotate, the analysis chamber 620 passes the detection point of the optical detection system 104, which is located at a fixed position. The optical detection system 104 may measure the optical absorbance (or light transmission) of the fluid mixture in the analysis chamber 620 as a function of radial distance R in the analysis chamber 620.

Figure 7:
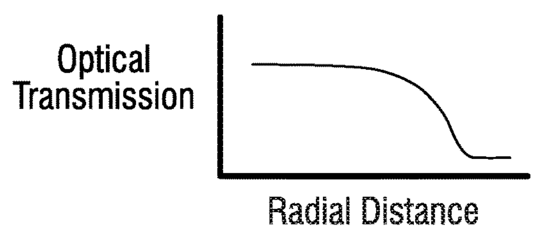
FIG. 7 is a representative graph showing optical transmission versus radial distance in an analysis chamber of a microfluidic device of FIG. 6.

The computer processing system 107 may output or store one or more graphs or traces, like that shown in FIG. 7 of the optical transmission as a function of radial distance R (FIG. 6). The optical absorbance may be measured periodically, such as once per revolution of the disc 102, to determine the effectiveness of the mixed inhibitor, as discussed above.

A comparison of graphs like that in FIG. 7, taken over a period of time, can indicate trends in the asphaltene sedimentation, as described above with respect to FIGS. 4A to 4F. For example, a good inhibitor will slow down asphaltene sedimentation, whereas a poor inhibitor will not slow down asphaltene sedimentation. By using the method of FIG. 8 batches of asphaltene inhibitors can be screened and appropriate concentrations selected.

Note that in addition to measuring and processing the optical absorbance (or light transmission) of the fluid mixture in the analysis chamber as a function of radial distance R in the analysis chamber and processing such absorbance/transmittance to characterize properties of the solid phase (e.g., asphaltenes) and the liquid phase (e.g., maltenes) within the analysis chamber as described herein, it will be appreciated that other optical measurements (such as light scattering, fluorescence, Raman scattering, and optical imaging) can be made on the fluid mixture in the analysis chamber as a function of radial distance R in the analysis chamber and such optical measurements can be processed to characterize properties of the solid phase (e.g., asphaltenes) and the liquid phase (e.g., maltenes) within the analysis chamber.

There have been described and illustrated herein several embodiments of a test apparatus and method that evaluates asphaltene inhibitors. While particular embodiments have been described herein with reference to particular means, materials and embodiments, it is not intended to be limited to the particulars described herein; rather it extends to all functionally equivalent structures, methods and uses as are within the scope of the appended claims. For example, while various embodiments make reference to asphaltene separation, it will be appreciated that the invention is broader and relates also to inhibition of organic and inorganic scale formation.

What is claimed is:

1. A centrifugal microfluidic system for evaluating fluid, the system including:

a microfluidic device configured to rotate about an axis and an optical detection system;

wherein the microfluidic device comprises an analysis chamber integral to the microfluidic device that is configured to separate a fluid into a solid phase and a liquid phase within the analysis chamber due to centrifugal force arising from rotation of the microfluidic device about a central axis; and wherein the optical detection system is configured to measure optical properties of the fluid within the analysis chamber in order to characterize properties of both the solid phase and liquid phase disposed within the analysis chamber.

2. The system of claim 1, wherein the microfluidic device comprises a sample reservoir for containing at least a sample and a precipitant reservoir for containing a precipitant, wherein the sample reservoir and the precipitant reservoir are fluidly coupled to the analysis chamber.

3. The system of claim 2, wherein the sample reservoir and the precipitant reservoir are positioned radially inward from the analysis chamber.

4. The system of claim 3, wherein the sample reservoir and the precipitant reservoir are configured to permit the sample and the precipitant to move toward the analysis chamber due to centrifugal force arising from rotation of the microfluidic device about the axis.

5. The system of claim 4, wherein the microfluidic device comprises a mixing chamber fluidly coupled between the sample reservoir and the precipitant reservoir and the analysis chamber.

6. The system of claim 5, wherein the mixing chamber is configured to receive the sample and the precipitant for mixing and to permit release of a mixture of the sample and the precipitant to the analysis chamber due to centrifugal force arising from rotation of the microfluidic device about the axis.

7. The system of claim 1, wherein the optical properties include at least one of light transmission, light scattering, fluorescence, Raman scattering, and optical imaging.

8. The system of claim 1, further comprising a motor to rotate the microfluidic device about the axis.

9. The system of claim 1, wherein the optical detection system is fixed with respect to the axis, and the optical detection system is optically coupled to the analysis chamber.

10. The system of claim 1, wherein the optical detection system is constructed to measure optical properties of fluid within the analysis chamber as a function of radial distance within the analysis chamber.

* * * * *